(12) United States Patent
Hynynen

(10) Patent No.: US 11,744,547 B2
(45) Date of Patent: Sep. 5, 2023

(54) PHASED ARRAY TRANSDUCER WITH COUPLING LAYER FOR SUPPRESSION OF GRATING LOBES

(71) Applicant: SUNNYBROOK RESEARCH INSTITUTE, Toronto (CA)

(72) Inventor: Kullervo Henrik Hynynen, Toronto (CA)

(73) Assignee: SUNNYBROOK RESEARCH INSTITUTE, Toronto (CA)

( * ) Notice: Subject to any disclaimer, the term of this patent is extended or adjusted under 35 U.S.C. 154(b) by 1021 days.

(21) Appl. No.: 16/066,865

(22) PCT Filed: Feb. 23, 2017

(86) PCT No.: PCT/CA2017/050229
§ 371 (c)(1),
(2) Date: Jun. 28, 2018

(87) PCT Pub. No.: WO2017/143443
PCT Pub. Date: Aug. 31, 2017

(65) Prior Publication Data
US 2019/0000416 A1 Jan. 3, 2019

Related U.S. Application Data

(60) Provisional application No. 62/298,850, filed on Feb. 23, 2016.

(51) Int. Cl.
*A61B 8/00* (2006.01)
*B06B 3/00* (2006.01)
(Continued)

(52) U.S. Cl.
CPC .......... *A61B 8/4281* (2013.01); *A61B 8/4488* (2013.01); *A61N 7/00* (2013.01);
(Continued)

(58) Field of Classification Search
CPC ...... A61B 8/4281; A61B 8/4488; A61N 7/00; A61N 2007/0078; B06B 3/00;
(Continued)

(56) References Cited

U.S. PATENT DOCUMENTS

| 6,027,457 A | * | 2/2000 | Shmulewitz | ......... | A61B 8/0833 600/437 |
| 2005/0101867 A1 | | 5/2005 | Johnson et al. | | |

(Continued)

OTHER PUBLICATIONS

Pubchem, "Compound Summary—Glycerol", 2020, PubChem (Year: 2020).*

(Continued)

*Primary Examiner* — Katherine L Fernandez
*Assistant Examiner* — Brooke Lyn Klein
(74) *Attorney, Agent, or Firm* — HILL & SCHUMACHER

(57) ABSTRACT

An ultrasound phased array transducer is disclosed that achieves suppression of grating lobes through the incorporation of a coupling layer, where the coupling layer is positioned adjacent to the phased array transducer such that an ultrasound beam propagates through the coupling layer prior to encountering a propagation medium. The phased-array elements may be provided such that one or both of the array pitch and a lateral extent of each ultrasound transducer element is larger than half of the ultrasound wavelength in the propagation medium. Grating lobes within the coupling layer and the propagation medium may be reduced or suppressed by selecting a coupling material having a speed of sound that exceeds that of the propagation medium. The coupling layer may have a thickness sufficient for the generation of a wavefront, and the coupling layer may be formed from a viscous or viscoelastic material.

30 Claims, 3 Drawing Sheets

(51) Int. Cl.
*G01S 7/52* (2006.01)
*G01S 15/89* (2006.01)
*A61N 7/00* (2006.01)
*G10K 11/26* (2006.01)

(52) U.S. Cl.
CPC ............ *B06B 3/00* (2013.01); *G01S 7/52077* (2013.01); *G01S 7/52079* (2013.01); *G01S 15/8915* (2013.01); *G10K 11/26* (2013.01); *A61N 2007/0078* (2013.01)

(58) Field of Classification Search
CPC ............ G01S 7/52077; G01S 7/52079; G01S 15/8915; G10K 11/26
See application file for complete search history.

(56) References Cited

U.S. PATENT DOCUMENTS

| | | | |
|---|---|---|---|
| 2008/0094300 A1* | 4/2008 | Lee | H01Q 21/065 343/844 |
| 2008/0094301 A1 | 4/2008 | Lee et al. | |
| 2008/0121040 A1* | 5/2008 | MacLauchlan | G01N 29/4463 73/618 |
| 2012/0165686 A1* | 6/2012 | Masuda | A61B 8/485 600/485 |
| 2012/0296215 A1 | 11/2012 | Brown et al. | |
| 2013/0090561 A1* | 4/2013 | Kusukame | G10K 11/02 600/443 |
| 2013/0301394 A1* | 11/2013 | Chen | B06B 1/0292 367/155 |

OTHER PUBLICATIONS

International Search Report PCT/CA2017/050229 dated Jun. 22, 2017.
Goss et al., IEEE Trans. Ultrason., Feerro. & Freq. Con. 43, 1111-1121 (1996).
Pernot et al., Phys Med Biol. 48, 2577-89 (2003).

* cited by examiner

PHASED ARRAY TRANSDUCER WITH COUPLING LAYER FOR SUPPRESSION OF GRATING LOBES

CROSS-REFERENCE TO RELATED APPLICATION

This application is a National Phase application claiming the benefit of the international PCT Patent Application No. PCT/CA2017/050229, filed on Feb. 23, 2017, in English, which claims priority to U.S. Provisional Application No. 62/298,850, titled "PHASED ARRAY TRANSDUCER WITH COUPLING LAYER FOR SUPPRESSION OF GRATING LOBES" and filed on Feb. 23, 2016, the entire contents of which are incorporated herein by reference.

BACKGROUND

The present disclosure relates to phased-array ultrasound devices.

Ultrasound phased-array systems employ an array of ultrasound elements that are excited using a pattern of delayed excitation signals that focus and steer the emitted ultrasound beam. By controlling the relative delays, the ultrasound beam can be scanned over a plurality of directions and/or focused to a plurality of locations. For example, in ultrasound imaging, a series of A-scans are collected by steering the ultrasound beam at different angles.

A small element-to-element pitch (typically $\lambda/2$) is conventionally required for phased array ultrasound transducers in order to avoid the generation of grating lobes, especially when the ultrasound beam is steered at large angles. This requirement leads to challenges in transducer fabrication, by placing constraints on the maximum transducer array element size (lateral extent). A larger irregular spacing may be employed to obtain a focused beam, provided that the element size is less or equal to $\lambda/2$, with a resulting cost of increased energy transmission through the near field. Although a fully populated array may be preferred, such a configuration comes with the cost of large number of elements for ultrasound applicators due to the short wavelength in the propagation medium.

SUMMARY

An ultrasound phased array transducer is disclosed that achieves suppression of grating lobes through the incorporation of a coupling layer, where the coupling layer is positioned adjacent to the phased array transducer such that an ultrasound beam propagates through the coupling layer prior to encountering a propagation medium. The phased-array elements may be provided such that one or both of the array pitch and a lateral extent of each ultrasound transducer element is larger than half of the ultrasound wavelength in the propagation medium. Grating lobes within the coupling layer and the propagation medium may be reduced or suppressed by selecting a coupling material having a speed of sound that exceeds that of the propagation medium. The coupling layer may have a thickness sufficient for the generation of a wavefront, and the coupling layer may be formed from a viscous or viscoelastic material.

Accordingly, in a first aspect, there is provided a phased array ultrasound transducer comprising:

an array of ultrasound transducer elements configured for emitting a phased-array ultrasound beam therefrom, wherein each ultrasound transducer element has an associated ultrasound emission wavelength in soft tissue, wherein a lateral extent of each transducer element is larger than half of the ultrasound wavelength in soft tissue; and a coupling layer contacting said array of ultrasound transducer elements, said coupling layer having a speed of sound greater than the speed of sound of soft tissue and a thickness sufficient for the generation of a wavefront therein, thereby reducing or suppressing the generation of grating lobes.

In another aspect, there is provided a phased array ultrasound transducer comprising:

an array of ultrasound transducer elements configured for emitting a phased-array ultrasound beam therefrom, wherein each ultrasound transducer element has an associated ultrasound emission wavelength in soft tissue, wherein a pitch of said array of ultrasound transducer elements is larger than half of the ultrasound wavelength in soft tissue; and a coupling layer contacting said plurality of ultrasound transducer elements, said coupling layer having a speed of sound greater than the speed of sound of soft tissue and a thickness sufficient for the generation of a wavefront therein, thereby reducing or suppressing the generation of grating lobes.

In another aspect, there is provided a method of generating a phased array ultrasound beam within a propagation medium, the method comprising:

providing an ultrasound transducer comprising:
an array of ultrasound transducer elements configured for emitting a phased-array ultrasound beam therefrom, wherein each ultrasound transducer element has an associated ultrasound emission wavelength in the propagation medium, wherein one or both of a pitch of said array of ultrasound transducer elements and a lateral extent of each ultrasound transducer element is larger than half of the ultrasound wavelength in the propagation medium; and
a coupling layer contacting said plurality of ultrasound transducer elements, said coupling layer having a speed of sound greater than the speed of sound of the propagation medium and a thickness sufficient for the generation of a wavefront therein, thereby reducing or suppressing the generation of grating lobes; and delivering beamformed signals to the transducer array elements, thereby generating an ultrasound beam that propagates through the coupling layer and into the propagation medium.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which.

DETAILED DESCRIPTION

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. Unless otherwise specified, the terms "about" and "approximately" mean plus or minus 25 percent or less.

It is to be understood that unless otherwise specified, any specified range or group is as a shorthand way of referring to each and every member of a range or group individually, as well as each and every possible sub-range or sub-group encompassed therein and similarly with respect to any sub-ranges or sub-groups therein. Unless otherwise specified, the present disclosure relates to and explicitly incorporates each and every specific member and combination of sub-ranges or sub-groups.

As used herein "viscoelastic" refers to a material having both viscous and elastic characteristics. A viscoelastic material deforms when subjected to stress, but when the stress is removed, only a fraction of the deformation remains. In various example embodiments, a viscoelastic material can be a solid, liquid, solution, or gel.

As used herein, the phrase "viscous material" refers to a liquid material with a viscosity between $10^2$ and $10^6$ cP at room temperature.

The present disclosure provides ultrasound phased array transducers that achieve suppression (e.g. reduction or elimination) of grating lobes through the incorporation of a coupling layer having a speed of sound that exceeds that of the propagation medium.

Figure 1:
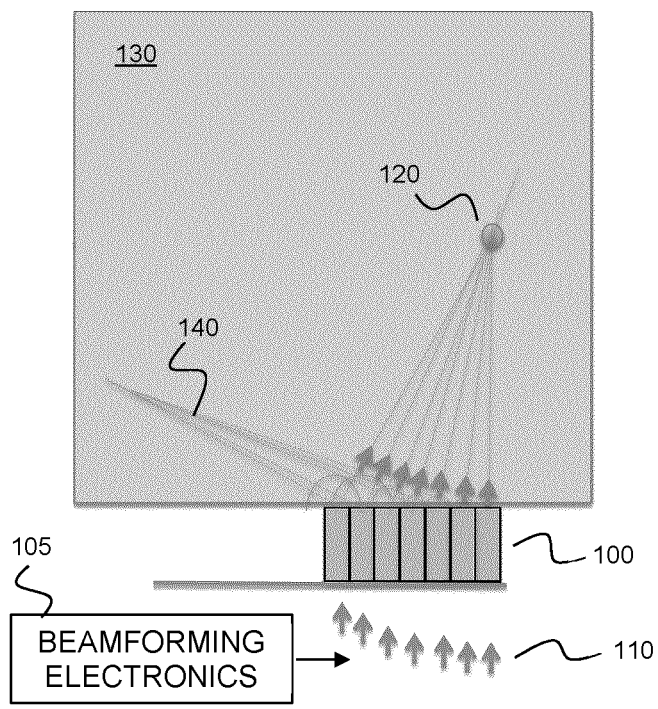
FIG. 1 shows the propagation of an ultrasound wavefront from phased array ultrasound transducers without a coupling layer.

Referring now to FIG. 1, a phased-array ultrasound transducer 100 is driven by beamforming electronics 105 (e.g. a transmit and optionally receive beamformer, with an optional Tx/Rx switch), which provides beamforming driving signals with relative temporal delays that cause the focusing of the emitted ultrasound wave at a focus 120 in the propagation medium 130 (e.g. tissue). In the embodiment shown in FIG. 1, the transducer pitch is greater than $\lambda/2$ (or, if the array is a sparse array, the element size is greater than $\lambda/2$), where $\lambda$ is the wavelength, associated with ultrasound generated by the array elements (e.g. corresponding to an acoustic resonant frequency), in the propagation medium, thereby resulting in the formation of a grating lobe 140.

Figure 2:
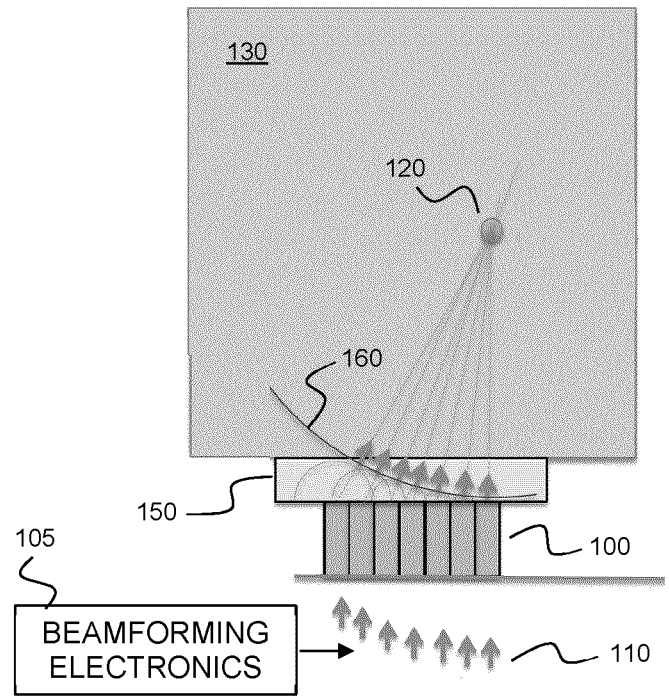
FIG. 2 shows the propagation of an ultrasound wavefront from phased array ultrasound transducers with a coupling layer, where the coupling layer is shown to suppress the generation of grating lobes.

FIG. 2 illustrates how the generation of grating lobes may be suppressed (e.g. reduced or eliminated) by the inclusion of a suitable coupling layer 150 in contact with the phased array. In the example embodiment shown, the coupling layer 150 is in contact with the distal surfaces of the ultrasound transducer array elements, and also in contact with the propagation medium 130, thereby facilitating coupling between the phased-array ultrasound transducer 100 and the propagation medium 130.

Unlike conventional acoustic coupling media, which are selected according to their relative acoustic impedances in order to suppress the reflection of acoustic energy at the interface with the propagation medium, the coupling layer 150 is selected to have a speed of sound that is greater than that of the propagation medium (the medium where the wave is to be transmitted). It is noted that the acoustic impedance of the coupling layer 150 may be less than, equal to, or greater than, that of the propagation medium, provided that the speed of sound of the coupling layer 150 exceeds that of the propagation medium 130.

The higher speed of sound of in the coupling layer 150 causes the wavelength within the coupling layer 150 to be larger than that of the propagation medium 130. As a result, the phased array element size can be increased from the conventional maximum value of $\lambda/2$ in the propagation medium since the value of $\lambda/2$ in the coupling layer is larger, while still avoiding the generation of grating lobes. The extent to which the array element size may be increased from the propagation medium wavelength depends on the difference between the speed of sound in the coupling layer 150 and the speed of sound in the propagation medium 130.

In one example embodiment, the phased array ultrasound elements may be provided such that a ratio of the lateral extent of each transducer element to half of the ultrasound wavelength in the propagation medium is less than the ratio of the speed of sound of the coupling layer to the speed of sound of the propagation medium.

In another example embodiment, the phased array ultrasound elements may be provided such that a ratio of the array pitch to half of the ultrasound wavelength in the propagation medium is less than the ratio of the speed of sound of the coupling layer to the speed of sound of the propagation medium.

In one example embodiment, the phased array ultrasound transducer may be provided such that the lateral extent (width) of each transducer element is at least two times the ultrasound wavelength in the propagation medium, and such that the speed of sound of the coupling layer is selected to at least twice as large as the one in the propagating medium to suppress the generation of grating lobes within the coupling layer.

In one example embodiment, the phased array ultrasound transducer may be provided such that the array pitch is at least two times the ultrasound wavelength in the propagation medium, and such that the speed of sound of the coupling layer is selected to at least twice as large as the one in the propagating medium to suppress the generation of grating lobes within the coupling layer.

The inclusion of the coupling layer with an increased speed of sound relative to the propagation medium may be employed to achieve a reduction in the number of array elements, and, accordingly, a reduction in the required RF-driving lines, relative to the number and array elements and RF-driving lines that would be needed if the phased array ultrasound transducer was directly coupled to the propagating medium. In an example implementation in which the propagation medium is tissue and the coupling layer has a sound speed of 3000 m/s, the centre-to-centre element spacing could be doubled while maintaining the same level of suppression of grating lobes, thus reducing the required channel number by a factor of four.

In some embodiments, the coupling layer material is selected to reduce or eliminate mechanical coupling between array elements. This may be achieved, for example, employing a coupling material that is viscous or viscoelastic. Non-limiting examples of suitable coupling materials include soft/flexible epoxies, soft polymers, rubbers, elastomers, composites, gels and liquids, provided that they satisfy the aforementioned criterion—i.e. the coupling material has a speed of sound that exceeds that of the propagation medium. For non-liquid coupling materials, the coupling layer could be attached to the phased array transducer via an adhesive (e.g. a glue). In another example implementation, a flexible polymer such as soft epoxy you could be directly coated onto the surface in a mold and then set (e.g. or cured).

In some example embodiments, the propagation medium is human tissue, which has an associated speed of sound of approximately 1540 m/s (e.g. in soft tissues). The speed of sound in various tissues is known to range from 1540 m/s (soft tissue), to 1585 m/s (muscle), to 1620 m/s (ocular tissue), to 4080 m/s (bone). The selection of the coupling material for use in biological studies or therapeutic treatments will therefore depend on the type of tissue. The selection of the coupling material may also depend on the angular range, relative to normal incidence, of the focused ultrasound beam.

Figure 3:
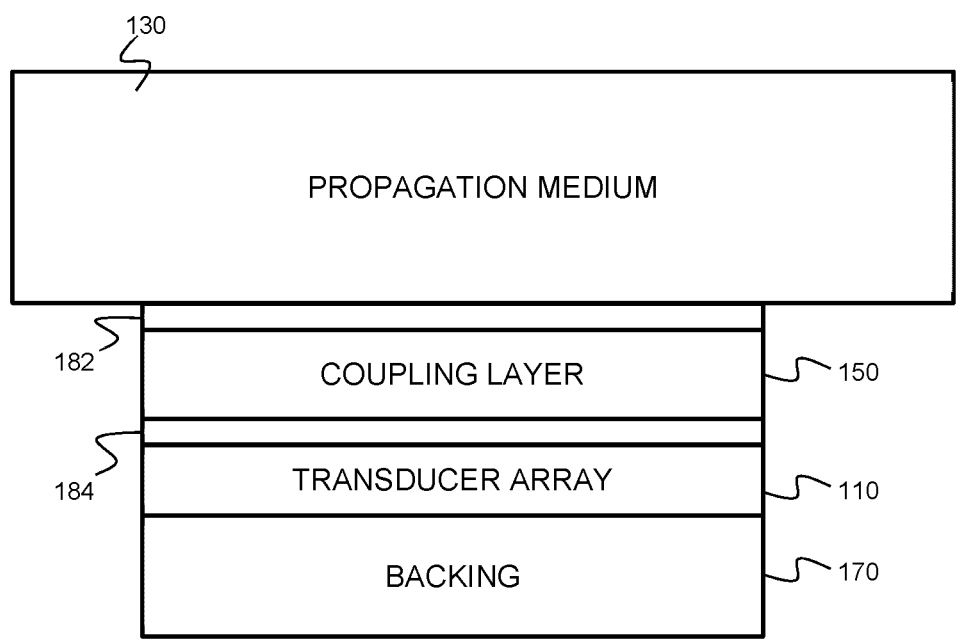
FIG. 3 shows an example phased array ultrasound transducer having a coupling layer and impedance matching layers.

Unlike conventional impedance matching layers, which typically have thicknesses of $\lambda/4$, the coupling layer is sufficiently thick to permit the formation of a wavefront. As shown in FIG. 1B, the coupling layer 150 has a sufficient thickness to support the formation of wavefront 160. The minimum thickness associated with this criterion may be determined, for example, based on computer simulations of the generated wavefront. Another example thickness criterion is that the coupling layer 150 is sufficiently thick to suppress the formation of grating lobes that would otherwise form if the transducer array elements were directly coupled to the propagation medium 130. A suitable thickness for satisfying this criterion may be determined, for example, based on computer simulations of the dependence of grating lobe formation on coupling layer thickness, or for example, by fabricating a set of transducers having coupling layers varying in thickness, and identifying a suitable minimum thickness for suppressing the formation of grating lobes, as per experimental measurements of the ultrasound beam profile. For example, a suitable minimal thickness for the coupling layer may be $\lambda$, $2\lambda$, $5\lambda$, or $10\lambda$, i.e. thickness values on the order of a wavelength within the coupling layer In some example embodiments, the acoustic impedance of the coupling layer 150 may be selected to be greater than that of the propagation layer, and less than that of the transducer material. FIG. 3 illustrates an example implementation in which one or more impedance matching layers are contacted with the coupling layer 150 in order to facilitate efficient coupling of ultrasound energy into the propagation medium. FIG. 3 also shows the optional inclusion of a backing contacting an opposing surface of the transducer array elements.

Figure 4:
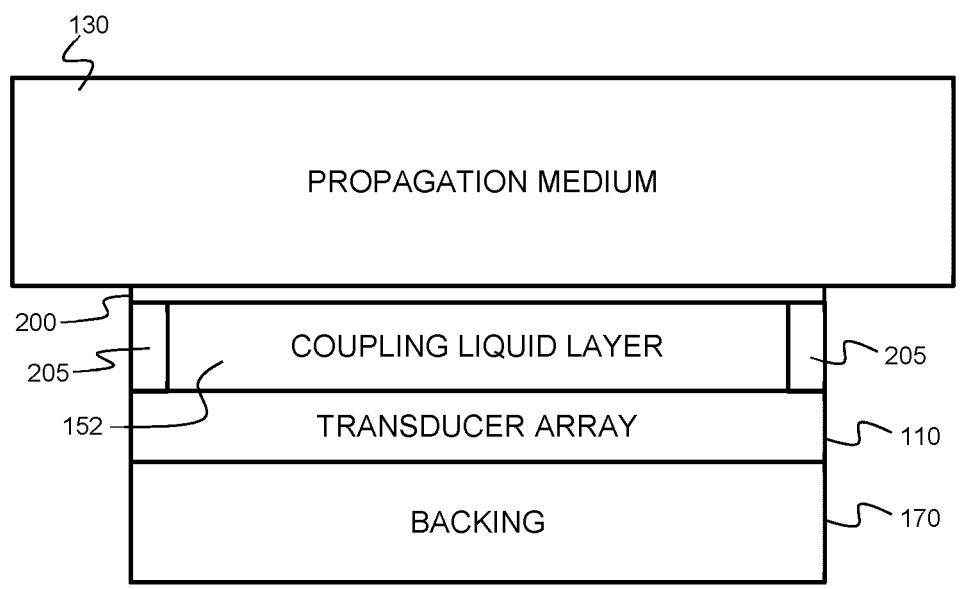
FIG. 4 shows an example phased array ultrasound transducer in which a liquid coupling layer is retained over the array elements via a membrane.

In one example implementation, the coupling layer may be a liquid medium, such as glycerol (speed of sound=1920 m/s at 25° C.). As shown in FIG. 4, a coupling liquid layer 152 may be retained by an enclosing or capping layer 200, such as a membrane (e.g. Kapton, mylar or PVDF). In the example embodiment illustrated in FIG. 4, a retaining membrane 200 is mechanically supported by a spacer 205. It will be understood that the configuration provided in FIG. 4 is merely one non-limiting example for retaining a liquid coupling layer over the phased array elements. In various non-limiting example embodiments, the speed of sound of the coupling layer is selected to be at least 2000 m/s, at least 2200 m/s, at least 2400 m/s, at least 2600 m/s, at least 2800 m/s, at least 3000 m/s, at least 3500 m/s, or at least 4000 m/s.

Although the phased array ultrasound transducer 100 is shown as a linear array of adjacent ultrasound array elements, it will be understood that the array elements phased array ultrasound transducer may form a sparse array.

In some example embodiments, the ultrasound elements of the phased array ultrasound transducer are mechanically de-coupled from one another, such as in the form of a kerfed array or a composite array, in which adjacent array elements are separated laterally by a filler for suppressing inter-element mechanical coupling. In other example embodiments, the phased array transducer may be a kerfless array.

The methods disclosed herein may be employed in a wide variety of ultrasound applications involving phased arrays, including, but not limited to, sonars, diagnostic and therapy ultrasound arrays, loud speaker arrays, and any other arrays generating any frequency of sound.

It may be useful for other phased arrays such as microwave, radio wave, and radar arrays.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

Therefore what is claimed is:

1. A phased array ultrasound transducer comprising:
an array of ultrasound transducer elements configured for emitting a phased-array ultrasound beam therefrom, wherein each ultrasound transducer element has an associated ultrasound emission wavelength in soft tissue, wherein a lateral extent of each transducer element is larger than half of the ultrasound wavelength in soft tissue; and
a coupling layer contacting said array of ultrasound transducer elements, said coupling layer having a speed of sound greater than a speed of sound of soft tissue and a thickness sufficient for generation of a wavefront therein, thereby reducing or suppressing generation of grating lobes;
wherein the thickness of said coupling layer exceeds an ultrasound wavelength in said coupling layer.

2. The phased array ultrasound transducer according to claim 1 wherein the speed of sound of said coupling layer is sufficiently high to eliminate the generation of grating lobes.

3. The phased array ultrasound transducer according to claim 1 wherein a ratio of the lateral extent of each transducer element to half of the ultrasound wavelength in soft tissue is less than a ratio of the speed of sound of the coupling layer to the speed of sound of tissue.

4. The phased array ultrasound transducer according to claim 1 wherein the speed of sound exceeds 2000 meters per second (m/s).

5. The phased array ultrasound transducer according to claim 1 wherein the lateral extent of each transducer element is at least two times the ultrasound wavelength in soft tissue, and wherein the speed of sound of said coupling layer is selected to at least twice as large as the speed of sound in tissue to suppress the generation of grating lobes within said coupling layer.

6. The phased array ultrasound transducer according to claim 1 wherein said coupling layer comprises a viscous or viscoelastic material.

7. The phased array ultrasound transducer according to claim 1 wherein said coupling layer is one of a liquid, gel and a viscoelastic polymer.

8. The phased array ultrasound transducer according to claim 1 wherein said coupling layer is comprises any one or more of flexible epoxy, flexible polymer, rubber, elastomer, and a composite.

9. The phased array ultrasound transducer according to claim 1 wherein said coupling layer comprises glycerol.

10. The phased array ultrasound transducer according to claim 1 wherein said coupling layer comprises a liquid, and wherein said liquid is retained in over said array of ultrasound transducer elements by a membrane.

11. The phased array ultrasound transducer according to claim 1 wherein said array of ultrasound transducer elements are spatially distributed as a sparse array.

12. The phased array ultrasound transducer according to claim 11 wherein a maximum element width is less than or equal to half of the ultrasound wavelength in soft tissue multiplied by a ratio of the speed of sound in the coupling layer and to the speed of sound in soft tissue.

13. A phased array ultrasound transducer comprising:
an array of ultrasound transducer elements configured for emitting a phased-array ultrasound beam therefrom, wherein each ultrasound transducer element has an associated ultrasound emission wavelength in soft tissue, wherein a pitch of said array of ultrasound transducer elements is larger than half of the ultrasound wavelength in soft tissue; and
a coupling layer contacting said plurality of ultrasound transducer elements, said coupling layer having a speed of sound greater than a speed of sound of soft tissue and a thickness sufficient for generation of a wavefront therein, thereby reducing or suppressing generation of grating lobes;
wherein the thickness of said coupling layer exceeds an ultrasound wavelength in said coupling layer.

14. The phased array ultrasound transducer according to claim 13 wherein the speed of sound of said coupling layer is sufficiently high to eliminate the generation of grating lobes.

15. The phased array ultrasound transducer according to claim 13 wherein a ratio of the pitch to half of the ultrasound wavelength in soft tissue is less than a ratio of the speed of sound of the coupling layer to the speed of sound of soft tissue.

16. The phased array ultrasound transducer according to claim 13 wherein the speed of sound exceeds 2000 meters per second (m/s).

17. The phased array ultrasound transducer according to claim 13 wherein the pitch is at least two times the ultrasound wavelength in soft tissue, and wherein the speed of sound of said coupling layer is selected to at least twice as large as the speed of sound in soft tissue to suppress the generation of grating lobes within said coupling layer.

18. The phased array ultrasound transducer according to claim 13 wherein said coupling layer comprises a viscous or viscoelastic material.

19. The phased array ultrasound transducer according claim 13 wherein said coupling layer is one of a liquid, gel and a viscoelastic polymer.

20. The phased array ultrasound transducer according to claim 13 wherein said coupling layer is comprises any one or more of flexible epoxy, flexible polymer, rubber, elastomer, and a composite.

21. The phased array ultrasound transducer according to claim 13 wherein said coupling layer comprises glycerol.

22. The phased array ultrasound transducer according to claim 13 wherein said coupling layer comprises a liquid, and wherein said liquid is retained in over said array of ultrasound transducer elements by a membrane.

23. A method of generating a phased array ultrasound beam within a propagation medium, the method comprising:
providing an ultrasound transducer comprising:
an array of ultrasound transducer elements configured for emitting a phased-array ultrasound beam therefrom, wherein each ultrasound transducer element has an associated ultrasound emission wavelength in the propagation medium, wherein one or both of a pitch of said array of ultrasound transducer elements and a lateral extent of each ultrasound transducer element is larger than half of the ultrasound wavelength in the propagation medium; and
a coupling layer contacting said plurality of ultrasound transducer elements, said coupling layer having a speed of sound greater than a speed of sound of the propagation medium and a thickness sufficient for generation of a wavefront therein, thereby reducing or suppressing generation of grating lobes, wherein the thickness of said coupling layer exceeds an ultrasound wavelength in said coupling layer; and
delivering beamformed signals to the transducer array elements, thereby generating an ultrasound beam that propagates through the coupling layer and into the propagation medium.

24. The method according to claim 23 wherein the speed of sound of said coupling layer is sufficiently high to eliminate the generation of grating lobes.

25. The method according to claim 23 wherein a ratio of the lateral extent of each transducer element to half of the ultrasound wavelength in the propagation medium is less than a ratio of the speed of sound of the coupling layer to the speed of sound of the propagation medium.

26. The method according to claim 23 wherein a ratio of the pitch to half of the ultrasound wavelength in the propagation medium is less than a ratio of the speed of sound of the coupling layer to the speed of sound of the propagation medium.

27. The method according to claim 23 wherein the speed of sound exceeds 2000 meters per second (m/s).

28. The method according to claim 23 wherein the lateral extent of each transducer element is at least two times the ultrasound wavelength in the propagation medium, and wherein the speed of sound of said coupling layer is selected to at least twice as large as the speed of sound in the propagation medium to suppress the generation of grating lobes within said coupling layer.

29. The method according to claim 23 wherein the pitch is at least two times the ultrasound wavelength in the propagation medium, and wherein the speed of sound of said coupling layer is selected to at least twice as large as the speed of sound in the propagation medium to suppress the generation of grating lobes within said coupling layer.

30. The method according to claim 23 wherein the coupling layer comprises a viscous or viscoelastic material.

* * * * *